United States Patent  
Cai et al.

(10) Patent No.: US 7,732,468 B2
(45) Date of Patent: Jun. 8, 2010

(54) 3-ARYL-6-ARYL-[1,2,4]TRIAZOLO[3,4-B][1,3,4]THIADIAZOLES AND RELATED COMPOUNDS AS ACTIVATORS OF CASPASES AND INDUCERS OF APOPTOSIS AND THE USE THEREOF

(75) Inventors: Sui Xiong Cai, San Diego, CA (US);
John A. Drewe, Carlsbad, CA (US);
Nilantha Sudath Sirisoma, San Diego, CA (US); Han-Zhong Zhang, San Diego, CA (US)

(73) Assignee: Cytovia, Inc., Tarrytown, NY (US)

( * ) Notice: Subject to any disclaimer, the term of this patent is extended or adjusted under 35 U.S.C. 154(b) by 106 days.

(21) Appl. No.: 11/984,296

(22) Filed: Nov. 15, 2007

(65) Prior Publication Data

US 2008/0113984 A1 May 15, 2008

Related U.S. Application Data

(60) Provisional application No. 60/858,936, filed on Nov. 15, 2006.

(51) Int. Cl.
*A61K 31/433* (2006.01)
*A61K 31/4196* (2006.01)
*C07D 513/04* (2006.01)

(52) U.S. Cl. .................. 514/363; 514/383; 548/136; 548/262.4

(58) Field of Classification Search .......... 514/363, 514/383; 548/262.4, 136
See application file for complete search history.

(56) References Cited

U.S. PATENT DOCUMENTS 7,144,876 B2  12/2006  Cai et al.
2004/0167192 A1  8/2004  Solow-Cordero et al.

FOREIGN PATENT DOCUMENTS

JP  2004-010548 A  1/2004

OTHER PUBLICATIONS

Kulkarni et al., Asian Journal of Chemistry (2003), 15(2), p. 621-624, (Abstract from STN).*
Invidata, F.P., et al., "Synthesis and Pharmacological Properties of 6-Substituted 3-(Pyridine-4-YL)-1,2,4-Triazole [3,4-b][1,3,4,]Thiadiazoles," *IL Farmaco 46*:1489-1495, Societá Chimica Italiana (1991).
Nadkarni, B.A., et al., "Synthesis and Anthelmintic Activity of 3,6-Disubstituted-7H-s-triazolo(3,4-b)(1,3,4)thiadiazines," *Arzneimittel-Forschung 51*:569-573, Editio Cantor Verlag (2001).
Xu, P.-F., et al., "Synthesis of Triazoles, Oxadiazoles and Condensed Heterocyclic Compounds Containing Cinchopheny and Studies on Biological Activity of Representative Compounds," *J. Chin. Chem. Soc. 51*:315-319, The Chemical Society, Taipei, Taiwan, Republic of China (2004).
Zhang, Z.-Y., and Xin, C., "Studies on Condensed Heteocyecic Compounds. I. Synthesis and Antibacterial Activity of 3-(4'-Pyridyl)-6-aryl-s-triazolo[3,4-b]-1,3,4-thiadiazoles," *Acta Chim. Sin. 49*:513-520, Science Press (1991) (English language abstract listed on the end page).
Dialog File 351, Accession No. 14013736, Derwent WPI English language abstract for JP 2004 010548 A (listed on accompanying PTO/SB/08A as document FP1).
Dincer, M., et al., "6-Phenyl-3-(4-pyridyl)-1,2,4-triazolo[3,4-b][1,3,4]thiadiazole," *Acta. Crystallogr. C 61*:o665-o667, Blackwell Publishing (2005).
Zhang, Q., et al., "Redifferentiation of human hepatoma cell induced by 6-(*p*-chlorophenyl)-3-[1-(*p*-chlorophenyl)-5-methyl-1*H*-1,2,3-triazol-4-yl]-s-triazolo[3,4-*b*]-1,3,4-thiadiazole (TDZ)," *Pharmazie 60*:378-382, Govi-Verlag Pharmazeutischer Verlag (2005).
International Search Report for International Application PCT/US07/23957, mailed on Apr. 23, 2008, United States Patent Office, Alexandria, Virginia.

* cited by examiner

*Primary Examiner*—Yong Chu
(74) *Attorney, Agent, or Firm*—Sterne, Kessler, Goldstein & Fox P.L.L.C.

(57) ABSTRACT

Disclosed are 3-aryl-6-aryl-7H-[1,2,4]triazolo[3,4-b][1,3,4]thiadiazoles and related compounds thereof, represented by the Formula I:

(I)

$$Ar_1 \text{—} \underset{X}{\overset{N-N}{\underset{N}{\bigsqcup}}} \text{—} Ar_2$$

wherein $Ar_1$, $Ar_2$, and $X$ are defined herein. The present invention relates to the discovery that compounds having Formula I are activators of caspases and inducers of apoptosis. Therefore, the activators of caspases and inducers of apoptosis of this invention may be used to induce cell death in a variety of clinical conditions in which uncontrolled growth and spread of abnormal cells occurs.

4 Claims, No Drawings

3-ARYL-6-ARYL-[1,2,4] TRIAZOLO[3,4-B][1,3,4]THIADIAZOLES AND RELATED COMPOUNDS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to 3-aryl-6-aryl-[1,2,4]triazolo[3,4-b][1,3,4]thiadiazoles and related compounds, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68.251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

C-Myc is a proto-oncogene and encodes the c-Myc transcription factor. Physiologically, cMyc expression correlates with cell proliferation in various cells and tissues of the body. cMyc is implicated in various biological processes including cell growth, proliferation, loss of differentiation and apoptosis. Deregulated expression of c-Myc occurs in a wide range of cancers and is often associated with poor prognosis suggesting an important role for this oncogene in tumor progression. Initially it was discovered in Burkitt's lymphoma as causative for the progression of the disease due to a translocation between chromosome 8 and the antibody-containing genes. More recently, cMyc has been detected in a wide range of cancers that include breast, colon, cervical, small-cell lung carcinomas, osteocarcomas, glioblastomas, melanoma and myeloid leukemias (Nesbit, C E et al. Oncogene, 18, 3004-3016 (1999); Blackwood, E. M et al. Science 251, 1211-1217 (1991); Mo H. & Henriksson M. *PNAS*, 103: 6344-6349 (2006)) Inactivation of c-Myc was found to cause tumor regression with rapid proliferation arrest and apoptosis in hematopoietic malignancies and osteosarcoma. Therefore inactivating cMyc or downstream targets of cMyc may provide important therapeutic advantages.

JP2004010548 disclosed fluorinated triazolothiadiazole compounds as electron-transporting agents.

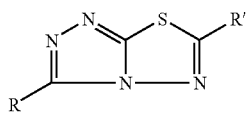

I

The fluorinated triazolothiadiazole compounds as represented by I (R, R'=pentafluoroalkyl, pentafluoroaryl) were disclosed to have excellent electron-transporting property.

Xu et al. (*Journal of the Chinese Chemical Society (Taipei, Taiwan)*, 51: 315-319 (2004)) reported the synthesis of heterocyclic derivatives, such as I (R=2-, 3-, 4-Cl, 3-, 4-F, 4-iodo, 3-, 4-Me, 3-, 4-Br). Some of the representative compounds were screened for antibacterial and fungicidal activity.

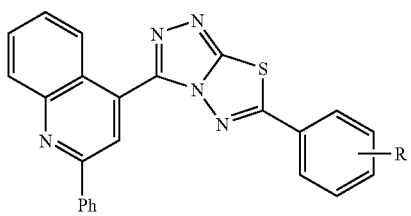

I

Invidiata et al. (*Farmaco* 46: 1489-95 (1991)) reported the synthesis and pharmacological properties of 6-substituted 3-(pyridin-4-yl)-1,2,4-triazole[3,4-b][1,3,4]thiadiazoles. A number of 6-substituted 3-(pyridine-4-yl)-1,2,4-triazole[3,4-b]thiadiazoles I (R=alkyl) were synthesized and evaluated for their pharmacological activity. Some of them exhibited moderate MAO, antimalarial and in vitro antitumor activity.

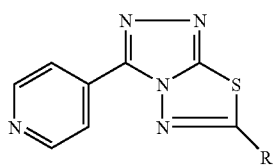

I

Zhang et al. (*Huaxue Xuebao*, 49: 513-20 (1991)) reported the synthesis and antibacterial activity of 3-(4-pyridyl)-6-aryl-s-triazolo[3,4-b]-1,3,4-thiadiazoles I (R=Me, MeO, $NO_2$, Br, Cl, F, I). Some of these compounds were screened for antibacterial activity against *Bacillus subtilis, Escherichia coli, Proteus vulgaris* and *Staphylococcus aureus*.

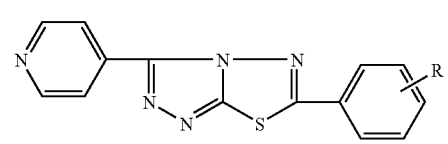

I

SUMMARY OF THE INVENTION

The present invention is related to the discovery that 3-aryl-6-aryl-[1,2,4]triazolo[3,4-b][1,3,4]thiadiazoles and related compounds, as represented in Formulae I-V, are activators of the caspase cascade and inducers of apoptosis. Thus, an aspect of the present invention is directed to the use of compounds of Formulae I-V as inducers of apoptosis.

A second aspect of the present invention is to provide a method for treating, preventing or ameliorating neoplasia and cancer by administering a compound of one of the Formulae I-V to a mammal in need of such treatment.

Many of the compounds within the scope of the present invention are novel compounds. Therefore, a third aspect of the present invention is to provide novel compounds of Formulae I-V, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of one of the Formulae I-V in admixture with one or more pharmaceutically acceptable carriers or diluents.

A fifth aspect of the present invention is directed to methods for the preparation of novel compounds of Formulae I-V.

DETAILED DESCRIPTION OF THE INVENTION

The present invention arises out of the discovery that 3-aryl-6-aryl-[1,2,4]triazolo[3,4-b][1,3,4]thiadiazoles and related compounds, as represented in Formulae I-V, are potent and highly efficacious activators of the caspase cascade and inducers of apoptosis. Therefore, compounds of Formulae I-V are useful for treating disorders responsive to induction of apoptosis.

Specifically, compounds of the present invention are represented by Formula I:

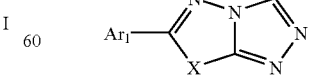

(I)

or pharmaceutically acceptable salts or prodrugs or tautomers thereof, wherein:

$Ar_1$ and $Ar_2$ independently are optionally substituted aryl or optionally substituted heteroaryl;

X is S, O or NR$_1$, wherein R$_1$ is hydrogen or an optionally substituted alkyl or aryl.

Preferred compounds of Formula I include compounds wherein Ar$_1$ and Ar$_2$ are phenyl, naphthyl, pyridyl, quinolyl, isoquinolyl, isoxazolyl, pyrazolyl, imidazolyl, thienyl, furyl, benzofuryl, 1,4,5,6-tetrahydrocyclopenta[c]pyrazol-3-yl, 1H-benzo[d]imidazolyl, indazolyl, indolyl or pyrrolyl, each of which is optionally substituted. More preferably, Ar$_1$ and Ar$_2$ are phenyl, 1,4,5,6-tetrahydrocyclopenta[c]pyrazol-3-yl or pyridyl. Another group of preferred compounds of Formula I include compounds wherein X is S or O. Another group of preferred compounds of Formula I include compounds wherein X is S.

One group of preferred compounds of the present invention are represented by Formulae II-IV:

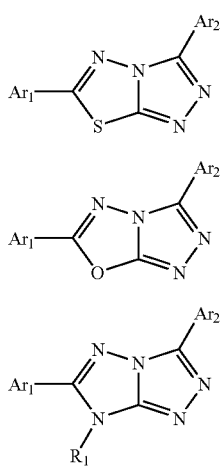

or pharmaceutically acceptable salts, prodrugs or tautomers thereof, wherein:

Ar$_1$ and Ar$_2$ independently are optionally substituted aryl or optionally substituted heteroaryl; and R$_1$ is hydrogen or an optionally substituted alkyl or aryl.

Preferred compounds of Formulae II-IV include compounds wherein Ar$_1$ and Ar$_2$ are phenyl, naphthyl, pyridyl, quinolyl, isoquinolyl, isoxazolyl, pyrazolyl, imidazolyl, thienyl, furyl, benzofuryl, 1,4,5,6-tetrahydrocyclopenta[c]pyrazol-3-yl, 1H-benzo[d]imidazolyl, indazolyl, indolyl or pyrrolyl, each of which is optionally substituted. More preferably, Ar$_1$ and Ar$_2$ are phenyl, 1,4,5,6-tetrahydrocyclopenta[c]pyrazol-3-yl or pyridyl.

Another group of preferred compounds of the present invention are represented by Formula V:

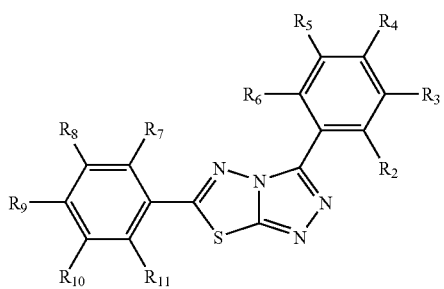

or pharmaceutically acceptable salts, prodrugs or tautomers thereof, wherein:

R$_2$-R$_{11}$ independently are hydrogen, halo, amino, alkoxy, C$_{1-10}$ alkyl, haloalkyl, aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, cyano, acylamido, hydroxy, thiol, sulfone, sulfoxide, acyloxy, azido, carboxy, methylenedioxy, carbonylamido or alkylthiol; or R$_2$ and R$_3$, or R$_3$ and R$_4$, or R$_4$ and R$_5$, or R$_5$ and R$_6$, or R$_7$ and R$_8$, or R$_8$ and R$_9$, or R$_9$ and R$_{10}$, or R$_{10}$ and R$_{11}$, taken together with the atoms to which they are attached to form an aryl, heteroaryl, partially saturated carbocyclic or partially saturated heterocyclic group, wherein said group is optionally substituted.

Preferred are compounds of Formula V, wherein R$_4$ and R$_5$, or R$_5$ and R$_6$, or R$_6$ and R$_7$, or R$_7$ and R$_8$, or R$_9$ and R$_{10}$, or R$_{10}$ and R$_{11}$, or R$_{11}$ and R$_{12}$, or R$_{12}$ and R$_{13}$, taken together to form a structure selected from the group consisting of —OCH$_2$O—, —(CH$_2$)$_3$—, —(CH$_2$)$_4$—, —OCH$_2$CH$_2$O—, —CH$_2$N(R$_{14}$)CH$_2$—, —CH$_2$CH$_2$N(R$_{14}$)CH$_2$—, —CH$_2$N(R$_{14}$)CH$_2$CH$_2$—, —N(R$_{14}$) CH=CH—, —CH=CH—N(R$_{14}$), —O—CH=CH—, —CH=CH—O—, —S—CH=CH—, —CH=CH—S— and —N=CH—CH=N—, wherein R$_{14}$ is hydrogen, C$_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Another group of preferred compounds are compounds of Formula V, wherein one of the R$_9$ and R$_{10}$ is an amino group.

Exemplary preferred compounds of Formulae I-V that may be employed in the method of the invention include, without limitation:

3-(3-Ethyl-1-methyl-1H-pyrazol-5-yl)-6-p-tolyl-[1,2,4] triazolo[3,4-b][1,3,4]thiadiazole;

3-(4-Chloro-3-ethyl-1-methyl-1H-pyrazol-5-yl)-6-(4-methoxyphenyl)-[1,2,4]triazolo[3,4-b][1,3,4]thiadiazole;

3-(3-Ethyl-1-methyl-1H-pyrazol-5-yl)-6-(4-methoxyphenyl)-[1,2,4]triazolo[3,4-b][1,3,4]thiadiazole;

6-(4-Diethylaminophenyl)-3-(pyridin-3-yl)-[1,2,4]triazolo[3,4-b][1,3,4]thiadiazole;

6-(3,4-Dimethoxyphenyl)-3-o-tolyl-[1,2,4]triazolo[3,4-b][1,3,4]thiadiazole;

3-(2-Chlorophenyl)-6-(3,4-dimethoxyphenyl)-[1,2,4]triazolo[3,4-b][1,3,4]thiadiazole;

6-(4-Diethylaminophenyl)-3-m-tolyl-[1,2,4]triazolo[3,4-b][1,3,4]thiadiazole;

6-(4-Bromophenyl)-3-(2-methoxyphenyl)-[1,2,4]triazolo[3,4-b][1,3,4]thiadiazole;

6-(3,4-Dimethoxyphenyl)-3-(2-methoxyphenyl)-[1,2,4] triazolo[3,4-b][1,3,4]thiadiazole;

6-(4-Diethylaminophenyl)-3-(pyridin-4-yl)-[1,2,4]triazolo[3,4-b][1,3,4]thiadiazole;

3-(2,4-Dichlorophenyl)-6-m-tolyl-[1,2,4]triazolo[3,4-b][1,3,4]thiadiazole;

3-(2-Chlorophenyl)-6-(3,4-methylenedioxyphenyl)-[1,2,4]triazolo[3,4-b][1,3,4]thiadiazole;

3-(4-Chlorophenyl)-6-(4-methoxyphenyl)-[1,2,4]triazolo[3,4-b][1,3,4]thiadiazole;

3-(2,4-Dichlorophenyl)-6-(3,4-dimethoxyphenyl)-[1,2,4] triazolo[3,4-b][1,3,4]thiadiazole;

3-(2-Chlorophenyl)-6-(4-ethoxyphenyl)-[1,2,4]triazolo [3,4-b][1,3,4]thiadiazole;

6-(4-Ethoxyphenyl)-3-o-tolyl-[1,2,4]triazolo[3,4-b][1,3,4]thiadiazole;

3-(2-Chlorophenyl)-6-(3,4-ethylenedioxyphenyl)-[1,2,4]triazolo[3,4-b][1,3,4]thiadiazole;

6-(Furan-2-yl)-3-(3,4,5-trimethoxyphenyl)-[1,2,4]triazolo[3,4-b][1,3,4]thiadiazole;

6-(4-Methoxyphenyl)-3-(3,4,5-trimethoxyphenyl)-[1,2,4]triazolo[3,4-b][1,3,4]thiadiazole;

6-(3,4-Dimethylphenyl)-3-(3,4,5-trimethoxyphenyl)-[1,2,4]triazolo[3,4-b][1,3,4]thiadiazole;

6-(3-Methoxyphenyl)-3-(3,4,5-trimethoxyphenyl)-[1,2,4]triazolo[3,4-b][1,3,4]thiadiazole;

6-(3,4-Dimethoxyphenyl)-3-(3,4,5-trimethoxyphenyl)-[1,2,4]triazolo[3,4-b][1,3,4]thiadiazole;

6-Phenyl-3-(3,4,5-trimethoxyphenyl)-[1,2,4]triazolo[3,4-b][1,3,4]thiadiazole;

6-(Pyridin-4-yl)-3-(3,4,5-trimethoxyphenyl)-[1,2,4]triazolo[3,4-b][1,3,4]thiadiazole;

6-(Thiophen-2-yl)-3-(3,4,5-trimethoxyphenyl)-[1,2,4]triazolo[3,4-b][1,3,4]thiadiazole;

3-(2-Chlorophenyl)-6-(4-methoxyphenyl)-[1,2,4]triazolo[3,4-b][1,3,4]thiadiazole;

6-(Benzofuran-2-yl)-3-(2-methoxyphenyl)-[1,2,4]triazolo[3,4-b][1,3,4]thiadiazole;

6-p-Tolyl-3-(3,4,5-trimethoxyphenyl)-[1,2,4]triazolo[3,4-b][1,3,4]thiadiazole;

3-(3,4-Dimethoxyphenyl)-6-(4-dimethylaminophenyl)-[1,2,4]triazolo[3,4-b][1,3,4]thiadiazole;

6-(4-Dimethylaminophenyl)-3-(3-methoxyphenyl)-1-[1,2,4]triazolo[3,4-b][1,3,4]thiadiazole;

3-(2-Chlorophenyl)-6-(4-dimethylaminophenyl)-[1,2,4]triazolo[3,4-b][1,3,4]thiadiazole;

6-(4-Diethylaminophenyl)-3-o-tolyl-[1,2,4]triazolo[3,4-b][1,3,4]thiadiazole;

3-(2-Chlorophenyl)-6-(4-diethylaminophenyl)-[1,2,4]triazolo[3,4-b][1,3,4]thiadiazole;

6-(4-Dimethylaminophenyl)-3-(pyridine-4-yl)-[1,2,4]triazolo[3,4-b][1,3,4]thiadiazole;

6-(4-Dimethylaminophenyl)-3-o-tolyl-[1,2,4]triazolo[3,4-b][1,3,4]thiadiazole;

3-(4-Dimethylaminophenyl)-6-(3-dimethylaminophenyl)-[1,2,4]triazolo[3,4-b][1,3,4]thiadiazole;

6-(4-Diethylaminophenyl)-3-(1,4,5,6-tetrahydrocyclopenta[c]pyrazol-3-yl)-[1,2,4]triazolo[3,4-b][1,3,4]thiadiazole;

6-(3,4-Dimethoxyphenyl)-3-(1,4,5,6-tetrahydrocyclopenta[c]pyrazol-3-yl)-[1,2,4]triazolo[3,4-b][1,3,4]thiadiazole;

6-(4-Methylphenyl)-3-(1,4,5,6-tetrahydrocyclopenta[c]pyrazol-3-yl)-[1,2,4]triazolo[3,4-b][1,3,4]thiadiazole;

6-(3-Amino-4-methylphenyl)-3-(3,4,5-trimethoxyphenyl)-[1,2,4]triazolo[3,4-b][1,3,4]thiadiazole;

6-(3-Amino-4-methylphenyl)-3-(2-methoxyphenyl)-[1,2,4]triazolo[3,4-b][1,3,4]thiadiazole;

6-(3-Amino-4-methoxyphenyl)-3-(2-methoxyphenyl)-[1,2,4]triazolo[3,4-b][1,3,4]thiadiazole;

3-(2-Methoxyphenyl)-6-(4-morpholinophenyl)-[1,2,4]triazolo[3,4-b][1,3,4]thiadiazole;

6-(1H-indazol-5-yl)-3-(2-methoxyphenyl)-[1,2,4]triazolo[3,4-b][1,3,4]thiadiazole;

6-(1H-indol-6-yl)-3-(2-methoxyphenyl)-[1,2,4]triazolo[3,4-b][1,3,4]thiadiazole;

and pharmaceutically acceptable salts or prodrugs thereof.

The present invention is also directed to novel compounds within the scope of Formulae I-V. Exemplary preferred compounds that may be employed in this invention include, without limitation:

6-(4-Methyl-3-nitrophenyl)-3-(3,4,5-trimethoxyphenyl)-[1,2,4]triazolo[3,4-b][1,3,4]thiadiazole;

6-(3-Amino-4-methylphenyl)-3-(3,4,5-trimethoxyphenyl)-[1,2,4]triazolo[3,4-b][1,3,4]thiadiazole;

6-(1H-Benzo[c]imidazol-6-yl)-3-(3,4,5-trimethoxyphenyl)-[1,2,4]triazolo[3,4-b][1,3,4]thiadiazole;

3-(2-Methoxyphenyl)-6-(4-methyl-3-nitrophenyl)-[1,2,4]triazolo[3,4-b][1,3,4]thiadiazole;

6-(3-Amino-4-methylphenyl)-3-(2-methoxyphenyl)-[1,2,4]triazolo[3,4-b][1,3,4]thiadiazole;

6-(4-Methoxy-3-nitrophenyl)-3-(2-methoxyphenyl)-[1,2,4]triazolo[3,4-b][1,3,4]thiadiazole;

6-(3-Amino-4-methoxyphenyl)-3-(2-methoxyphenyl)-[1,2,4]triazolo[3,4-b][1,3,4]thiadiazole;

6-(4-Morpholinophenyl)-3-(3,4,5-trimethoxyphenyl)-[1,2,4]triazolo[3,4-b][1,3,4]thiadiazole;

3-(2-Methoxyphenyl)-6-(4-morpholinophenyl)-[1,2,4]triazolo[3,4-b][1,3,4]thiadiazole;

6-(3-Methoxy-4-nitrophenyl)-3-(2-methoxyphenyl)-[1,2,4]triazolo[3,4-b][1,3,4]thiadiazole;

3-(2-Methoxyphenyl)-6-(pyridin-3-yl)-[1,2,4]triazolo[3,4-b][1,3,4]thiadiazole;

6-(1H-indazol-5-yl)-3-(2-methoxyphenyl)-[1,2,4]triazolo[3,4-b][1,3,4]thiadiazole;

6-(1H-indol-6-yl)-3-(2-methoxyphenyl)-[1,2,4]triazolo[3,4-b][1,3,4]thiadiazole;

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl, and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl, and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino and optionally substituted amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl, alkoxy, alkylthio, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl ($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, methylenedioxy, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$) alkenyl, $C_6$-$C_{10}$ aryl($C_2$-$C_6$)alkynyl, $C_1$-$C_6$ hydroxyalkyl, morpholino, nitro, amino, ureido, cyano, $C_1$-$C_6$ acylamino, hydroxy, thiol, sulfone, sulfoxide, $C_1$-$C_6$ acyloxy, azido, $C_1$-$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl, and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl, and cycloheptyl.

Useful saturated or partially saturated carbocyclic groups are cycloalkyl groups as described above, as well as cycloalkenyl groups, such as cyclopentenyl, cycloheptenyl, and cyclooctenyl.

Useful halo or halogen groups include fluorine, chlorine, bromine, and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl, or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms.

Useful heteroaryl groups include thienyl (thiophenyl), benzo[b]thienyl, naphtho[2,3-b]thienyl, thianthrenyl, furyl (furanyl), pyranyl, benzofuranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthpyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, 1,4,5,6-tetrahydrocyclopenta[c]pyrazolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy, and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I, II and V could be prepared as illustrated by the exemplary reaction in Scheme 1. Reaction of 4-amino-5-(3-chloro-4,5-dimethoxyphenyl)-3-mercapto-4H-1,2,4-triazole with 4-dimethylaminobenzoic acid in POCl₃ should produce 6-(4-dimethylaminophenyl)-3-(3-chloro-4,5-dimethoxyphenyl)-[1,2,4]triazolo[3,4-b][1,3,4]thiadiazole.

Compounds of this invention with Formulae I, II and V also could be prepared as illustrated by the exemplary reaction in Scheme 2. Reaction of 4-amino-5-(2-methoxyphenyl)-3-mercapto-4H-1,2,4-triazole with 4-methyl-3-nitrobenzoyl chloride in POCl₃ produced 6-(4-methyl-3-nitrophenyl)-3-(2-methoxyphenyl)-[1,2,4]triazolo[3,4-b][1,3,4]thiadiazole. Reduction of the nitro group using SnCl₂ produced 6-(3-amino-4-methylphenyl)-3-(2-methoxyphenyl)-[1,2,4]triazolo[3,4-b][1,3,4]thiadiazole.

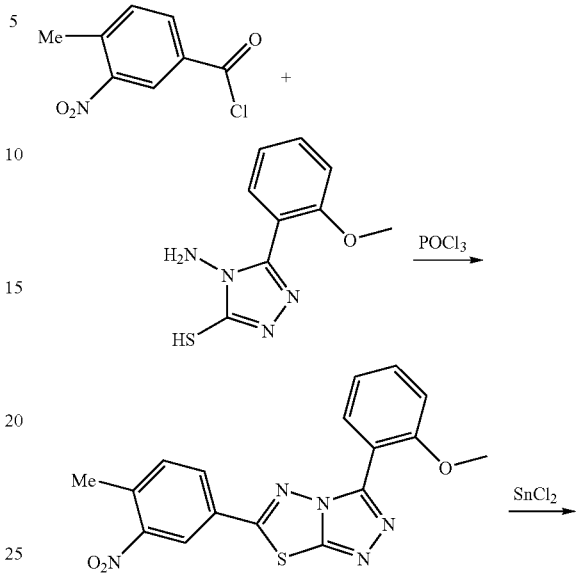

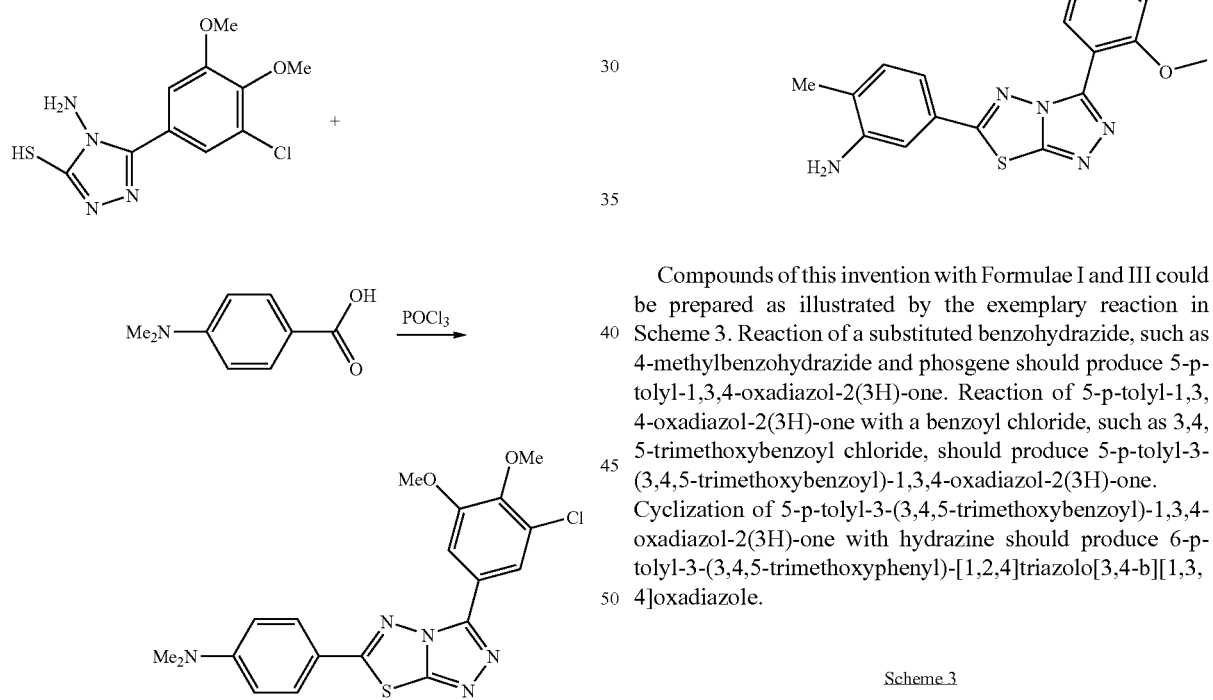

Compounds of this invention with Formulae I and III could be prepared as illustrated by the exemplary reaction in Scheme 3. Reaction of a substituted benzohydrazide, such as 4-methylbenzohydrazide and phosgene should produce 5-p-tolyl-1,3,4-oxadiazol-2(3H)-one. Reaction of 5-p-tolyl-1,3,4-oxadiazol-2(3H)-one with a benzoyl chloride, such as 3,4,5-trimethoxybenzoyl chloride, should produce 5-p-tolyl-3-(3,4,5-trimethoxybenzoyl)-1,3,4-oxadiazol-2(3H)-one. Cyclization of 5-p-tolyl-3-(3,4,5-trimethoxybenzoyl)-1,3,4-oxadiazol-2(3H)-one with hydrazine should produce 6-p-tolyl-3-(3,4,5-trimethoxyphenyl)-[1,2,4]triazolo[3,4-b][1,3,4]oxadiazole.

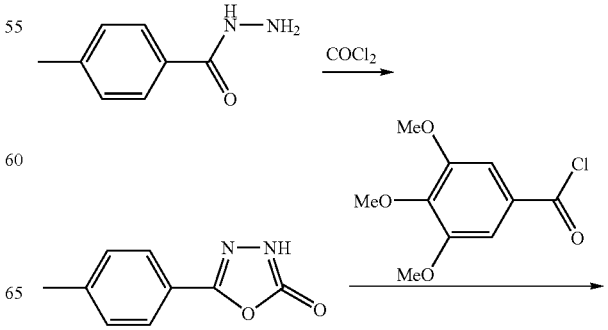

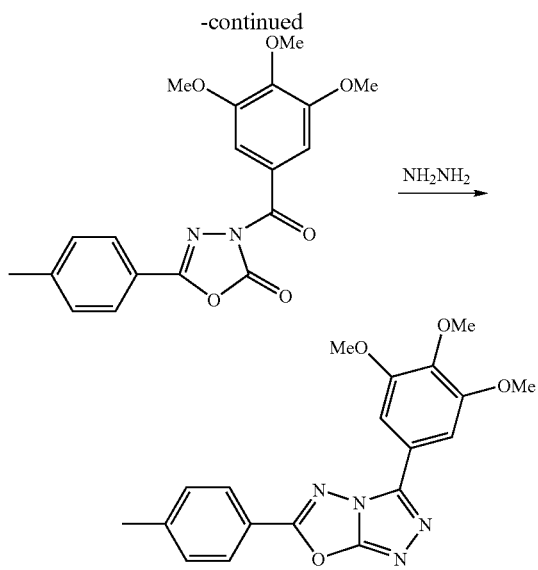
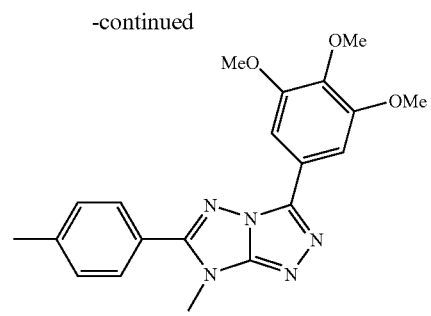

Compounds of this invention with Formulae I and IV could be prepared as illustrated by the exemplary reaction in Scheme 4. Treatment of a substituted benzoyl semicarbazide, such as 1-(4-methylbenzoyl)-4-methyl-semicarbazide with a base such as NaOH should produce 4-methyl-5-p-tolyl-2H-1,2,4-triazol-3(4H)-one. Reaction of 4-methyl-5-p-tolyl-2H-1,2,4-triazol-3(4H)-one with a benzoyl chloride, such as 3,4,5-trimethoxybenzoyl chloride, should produce 4-methyl-5-p-tolyl-2-(3,4,5-trimethoxybenzoyl)-2H-1,2,4-triazol-3(4H)-one. Cyclization of 4-methyl-5-p-tolyl-2-(3,4,5-trimethoxybenzoyl)-2H-1,2,4-triazol-3(4H)-one with hydrazine should produce 7-methyl-6-p-tolyl-3-(3,4,5-trimethoxyphenyl)-7H-[1,2,4]triazolo[5,1-c][1,2,4]triazole.

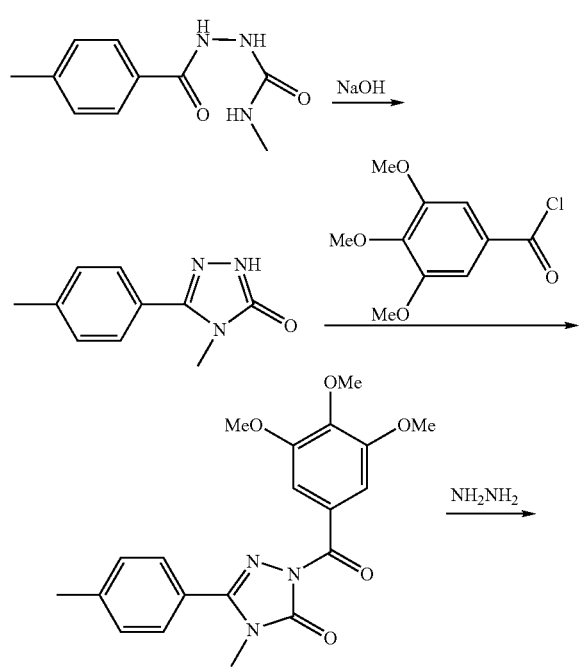

An important aspect of the present invention is the discovery that compounds having Formulae I-V are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I-V are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer, such as breast cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I-V, which functions as a caspase cascade activator and inducer of apoptosis.

The present invention also includes a therapeutic method comprising administering to an animal an effective amount of a compound, or a pharmaceutically acceptable salt or prodrug of said compound of Formulae I-V, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound, or a pharmaceutically acceptable salt of said compound of Formulae I-V, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-V, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but not are limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies, such as campath, Trastuzumab (Herceptin®) or Rituximab (Rituxan®). Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., *Cancer Res* 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., *Cancer Res.* 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res.* 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin, and cerivastatin.

It has been reported that HIV protease inhibitors, such as indinavir or saquinavir, have potent anti-angiogenic activities and promote regression of Kaposi sarcoma (Sgadari, C., et al., *Nat. Med.* 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol.* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, Such as STI571 (Imatinib mesilate, Gleevec®), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known tyrosine kinase inhibitor, or a pharmaceutically acceptable salt of said agent. Examples of known tyrosine kinase inhibitors, which can be used for combination therapy include, but are not limited to, Gleevec®, ZD1839 (Iressa), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611, and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine, and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology* (*Huntingt*) 16 (No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operates rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-V, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgaris. Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-V, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-V, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-V, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiescence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al.

*Hepatology* 3:656-64 (2000)). Therefore, apoptosis inducers are useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine, and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid, or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxy-propylmethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400), or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments, and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

6-(4-Methyl-3-nitrophenyl)-3-(3,4,5-trimethoxyphenyl)-[1,2,4]triazolo[3,4-b][1,3,4]thiadiazole A mixture of 4-amino-3-mercapto-5-(3,4,5-trimethoxyphenyl)-4H-1,2,4-triazole (220 mg, 0.78 mmol) and 4-methyl-3-nitrobenzoyl chloride (156 mg, 0.78 mmol) in phosphoryl chloride (2 mL) was refluxed for 3 h. The solvent was evaporated and the residue was dissolved in dichloromethane (20 mL). It was neutralized by aqueous sodium carbonate. The organic layer was dried over sodium sulfate, and concentrated to give 293 mg (85%) of the title compound as solid. $^1$H NMR (CDCl$_3$): 8.59 (d, J=2.1 Hz, 1H), 8.05-8.01 (dd, J=7.8, 1.8 Hz, 1H), 7.73 (s, 1H), 7.62 (d, J=8.1 Hz, 1H), 4.02 (s, 6H), 3.95 (s, 3H), 2.75 (s, 3H).

EXAMPLE 2

6-(3-Amino-4-methylphenyl)-3-(3,4,5-trimethoxyphenyl)-[1,2,4]triazolo[3,4-b][1,3,4]thiadiazole A mixture of 6-(4-methyl-3-nitrophenyl)-3-(3,4,5-trimethoxyphenyl)-[1,2,4]triazolo[3,4-b][1,3,4]thiadiazole (256 mg, 0.6 mmol) and tin(II) chloride (675 mg, 3 mmol) in methanol (25 mL) was refluxed under argon for 6 h. It was then diluted with water (30 mL) and neutralized with 2N aqueous sodium hydroxide to pH=12, and extracted with ethyl acetate (3×20 mL). The extracts were dried, concentrated and the residue was purified by column chromatography (EtOAc as eluent) to give 66 mg (28%) of the title compound as solid. $^1$H NMR (CDCl$_3$): 7.71 (s, 2H), 7.23 (m, 2H), 7.17 (s, 1H), 4.00 (s, 6H), 3.94 (s, 3H), 2.26 (s, 3H).

EXAMPLE 3

6-(1H-Benzo[d]imidazol-6-yl)-3-(3,4,5-trimethoxyphenyl)-[1,2,4]triazolo[3,4-b][1,3,4]thiadiazole A mixture of 4-amino-3-mercapto-5-(3,4,5-trimethoxyphenyl)-4H-1,2,4-triazole (80 mg, 0.28 mmol) and 3H-benzo[d]imidazole-5-carboxylic acid (46 mg, 0.28 mmol) in phosphoryl chloride (2 mL) was refluxed for 3 h. The solvent was evaporated and the residue was dissolved in dichloromethane (20 mL). It was neutralized with aqueous sodium carbonate. The organic layer was dried over sodium sulfate, concentrated to give 20 mg (17%) of the title compound as a solid. $^1$H NMR (CD$_3$OD): 8.55 (s, 1H), 8.35 (s, 1H), 8.01-7.85 (m, 2H), 7.72 (s, 1H), 3.99 (s, 6H), 3.87 (s, 3H).

EXAMPLE 4

3-(2-Methoxyphenyl)-6-(4-methyl-3-nitrophenyl)-[1,2,4]triazolo[3,4-b][1,3,4]thiadiazole The title compound was prepared in a manner similar to example 1. From 4-amino-3-mercapto-5-(2-methoxyphenyl)-4H-1,2,4-triazole (333 mg, 1.5 mmol) and 4-methyl-3-nitrobenzoyl chloride (299 mg, 1.5 mmol) was obtained 450 mg (82%) of the title compound as a solid. $^1$H NMR (CD$_3$OD): 8.61 (d, J=1.8 Hz, 1H), 8.26-8.22 (dd, J=8.4, 2.1 Hz, 1H), 7.92-7.88 (m, 1H), 7.79-7.76 (d, J=8.1 Hz, 1H), 7.78-7.68 (m, 1H), 7.37 (d, J=8.1 Hz, 1H), 7.28 (t, J=6.0 Hz, 1H), 4.00 (s, 3H), 2.75 (s, 3H).

EXAMPLE 5

6-(3-Amino-4-methylphenyl)-3-(2-methoxyphenyl)-[1,2,4]triazolo[3,4-b][1,3,4]thiadiazole The title compound was prepared in a manner similar to example 2. From 3-(2-methoxyphenyl)-6-(4-methyl-3-nitrophenyl)-[1,2,4]triazolo[3,4-b][1,3,4]thiadiazole (367 mg, 1.0 mmol) and tin chloride (1.66 g, 5 mmol) was obtained 187 mg (55%) of the title compound as a solid. $^1$H NMR (CDCl$_3$): 7.82-7.79 (dd, J=7.5, 1.8 Hz, 1H), 7.56-7.50 (m, 1H), 7.17-7.09 (m, 5H), 3.91 (s, 3H), 2.23 (s, 3H).

EXAMPLE 6

6-(4-Methoxy-3-nitrophenyl)-3-(2-methoxyphenyl)-[1,2,4]triazolo[3,4-b][1,3,4]thiadiazole The title compound was prepared in a manner similar to example 3. From 4-amino-3-mercapto-5-(2-methoxyphenyl)-4H-1,2,4-triazole (333 mg, 1.5 mmol) and 4-methoxy-3-nitrobenzoic acid (296 mg, 1.5 mmol) was obtained 430 mg (75%) of the title compound as a solid. $^1$H NMR (CD$_3$OD): 8.40 (s, 1H), 8.04-8.22 (m, 1H), 7.78 (m, 1H), 7.56 (m, 1H), 7.28-7.05 (m, 3H), 4.07 (s, 3H), 3.89 (s, 3H).

EXAMPLE 7

6-(3-Amino-4-methoxyphenyl)-3-(2-methoxyphenyl)-[1,2,4]triazolo[3,4-b][1,3,4]thiadiazole The title compound was prepared in a manner similar to example 2. From 6-(4-methoxy-3-nitrophenyl)-3-(2-methoxyphenyl)-[1,2,4]triazolo[3,4-b][1,3,4]thiadiazole (352 mg, 0.92 mmol) and tin chloride (1.03 g, 4.6 mmol) was obtained 276 mg (85%) of the title compound as a solid. $^1$H NMR (CDCl$_3$): 7.82-7.79 (dd, J=7.5, 1.8 Hz, 1H), 7.56-7.48 (m, 1H), 7.24-7.19 (m, 4H), 6.86-6.83 (d, J=8.1 Hz, 1H), 4.00 (bs, 2H), 3.93 (s, 3H), 3.91 (s, 3H).

EXAMPLE 8

6-(4-Morpholinophenyl)-3-(3,4,5-trimethoxyphenyl)-[1,2,4]triazolo[3,4-b][1,3,4]thiadiazole A mixture of 4-morpholinobenzoic acid (86 mg, 0.42 mmol) and 4-amino-3-mercapto-5-(3,4,5-trimethoxyphenyl)-4H-1,2,4-triazole (102 mg, 0.36 mmol) was refluxed in POCl$_3$ (5 mL) for 2 h. The reaction mixture was cooled to room temperature and excess POCl$_3$ was removed under vacuum. The residue was dissolved in ethyl acetate and washed with saturated NaHCO$_3$. The organic layer was dried over anhydrous Na$_2$SO$_4$, filtered and concentrated. The crude product was purified by chromatography (80% ethyl acetate/hexane; 1 mL methanol/100 mL of solvent) to give the title compound as a yellow solid (40 mg, 0.088 mmol, 24%). $^1$H NMR (CDCl$_3$): 7.78 (m, 2H), 7.73 (s, 2H), 6.98 (m, 2H), 4.00 (s, 6H), 3.94 (s, 3H), 3.89 (m, 4H), 3.41 (m, 4H).

EXAMPLE 9

3-(2-Methoxyphenyl)-6-(4-morpholinophenyl)-[1,2,4]triazolo[3,4-b][1,3,4]thiadiazole The title compound was prepared in a manner similar to example 8. From 4-morpholinobenzoic acid (87 mg, 0.42 mmol) and 4-amino-3-mercapto-5-(2-methoxyphenyl)-4H-1,2,4-triazole (98 mg, 0.44 mmol) was obtained the title compound as a yellow solid (163 mg, 0.41 mmol, 97%). $^1$H NMR (CDCl$_3$): 7.82 (dd, J=7.8, 1.8 Hz, 1H), 7.73 (m, 2H), 7.51 (ddd, J=8.1, 7.2, 1.5 Hz, 1H), 7.08-7.15 (m, 2H), 6.91 (m, 2H), 3.91 (s, 3H), 3.86 (m, 4H), 3.29 (m, 4H).

EXAMPLE 10

6-(3-Methoxy-4-nitrophenyl)-3-(2-methoxyphenyl)-[1,2,4]triazolo[3,4-b][1,3,4]thiadiazole The title compound was prepared in a manner similar to example 8. From 3-methoxy-4-nitrobenzoic acid (216 mg, 0.972 mmol) and 4-amino-3-mercapto-5-(2-methoxyphenyl)-4H-1,2,4-triazole (208 mg, 1.06 mmol) was obtained the title compound as a light yellow solid (259 mg, 0.68 mmol, 69%). $^1$H NMR (DMSO-d$_6$): 8.09 (d, J=8.7 Hz, 1H), 7.74 (d, J=1.8 Hz, 1H), 7.60-7.74 (m, 3H), 7.31 (d, J=8.4 Hz, 1H), 7.17 (dt, J=7.2, 0.6 Hz, 1H), 4.05 (s, 3H), 3.88 (s, 3H).

EXAMPLE 11

3-(2-Methoxyphenyl)-6-(pyridin-3-yl)-[1,2,4]triazolo[3,4-b][1,3,4]thiadiazole

The title compound was prepared in a manner similar to example 8. From nicotinic acid (172 mg, 1.39 mmol) and 4-amino-3-mercapto-5-(2-methoxyphenyl)-4H-1,2,4-triazole (320 mg, 1.44 mmol) was obtained the title compound as an off-white solid (395 mg, 1.28 mmol, 91%). $^1$H NMR (DMSO-d$_6$): 9.12 (d, J=2.4 Hz, 1H), 8.83 (dd, J=5.1, 1.8 Hz, 1H), 8.35 (m, 1H), 7.65 (m, 3H), 7.30 (d, J=8.1, 1H), 7.17 (dt, J=7.2, 0.6 Hz, 1H), 3.87 (s, 3H).

EXAMPLE 12

6-(1H-indazol-5-yl)-3-(2-methoxyphenyl)-[1,2,4]triazolo[3,4-b][1,3,4]thiadiazole The title compound was prepared in a manner similar to example 3. From 4-amino-3-mercapto-5-(2-methoxyphenyl)-4H-1,2,4-triazole (222 mg, 1.0 mmol) and 1H-indazole-5-carboxylic acid hydrochloride (199 mg, 1.0 mmol) was obtained 65 mg (19%) of the title compound as a solid. $^1$H NMR (CD$_3$OD): 8.48 (s, 1H), 8.24 (s, 1H), 8.04-8.00 (dd, J=9.0, 1.8 Hz, 1H), 7.84 (dd, J=9.0, 1.5 Hz, 1H), 7.74-7.71 (d, J=9.6 Hz), 7.67-7.62 (m, 1H), 7.28 (d, J=8.7 Hz, 1H), 7.20 (t, J=7.2 Hz, 1H), 3.98 (s, 3H).

EXAMPLE 13

6-(1H-indol-6-yl)-3-(2-methoxyphenyl)-[1,2,4]triazolo[3,4-b][1,3,4]thiadiazole

The title compound was prepared in a manner similar to example 8. From 1H-indole-6-carboxylic acid (120 mg, 0.74 mmol) and 4-amino-3-mercapto-5-(2-methoxyphenyl)-4H-1,2,4-triazole (175 mg, 0.79 mmol) was obtained the title compound as an off-white solid (38 mg, 0.11 mmol, 15%). $^1$H NMR (CDCl$_3$/D$_4$-Methanol): 9.94 (s, broad, 1H), 7.95 (t, J=0.9 Hz, 1H), 7.83 (dd, J=7.8, 1.8 Hz, 1H), 7.72 (d, J=8.4 Hz, 1H), 7.61 (dd, J=8.1 Hz, 1.8, 1H), 7.55 (m, 1H), 7.41 (t, J=3.0 Hz, 1H), 7.13 (m, 2H), 6.61 (m, 1H), 3.93 (s, 3H).

EXAMPLE 14

Identification of 6-(3,4-Dimethoxyphenyl)-3-(2-methoxyphenyl)-[1,2,4]triazolo[3,4-b][1,3,4]thiadiazole and Analogs as Caspase Cascade Activators and Inducers of Apoptosis in Solid Tumor Cells Human breast cancer cell lines T-47D, human hepatocellular carcinoma cell line SNU398, human colon carcinoma cell line HCT116, human cancer cell line H1299, human Burkitt's lymphoma cell line Namalwa, human lymphoma cell line Raji, and human B cell lymphoblastoid cell line Ramos were grown according to media component mixtures designated by American Type Culture Collection+10% FCS (Invitrogen Corporation), in a 5% $CO_2$-95% humidity incubator at 37° C. T-47D and H1299 cells were maintained at a cell density between 50 and 80% confluency at a cell density of 0.1 to $0.6 \times 10^6$ cells/mL. Cells were harvested at 600×g and resuspended at $0.65 \times 10^6$ cells/mL into appropriate media+ 10% FCS. An aliquot of 22.5 µL of cells was added to a well of a 384-well microtiter plate containing 2.5 µL of a 10% DMSO in RPMI-1640 media solution containing 0.16 to 100 µM of 6-(3,4-dimethoxyphenyl)-3-(2-methoxyphenyl)-[1,2,4]triazolo[3,4-b][1,3,4]thiadiazole or other test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 µL of a solution containing 14 µM of N-(Ac-DEVD)-N'-ethoxycarbonyl-R110 (SEQ ID No.:1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - Control\ RFU_{(T=0)} = Net\ RFU_{(T=3h)}$$

The activity of caspase cascade activation was determined by the ratio of the net RFU value for 6-(3,4-dimethoxyphenyl)-3-(2-methoxyphenyl)-[1,2,4]triazolo[3,4-b][1,3,4]thiadiazole (Example I) or other test compound to that of control samples. The $EC_{50}$ (nM) was determined by a sigmoidal dose-response calculation (Prism 3.0, GraphPad Software Inc.).

The caspase potency ($EC_{50}$) are summarized in Table I:

| Entry | Structure | $EC_{50}$ (nM) | | | | | | |
|---|---|---|---|---|---|---|---|---|
| | | T47D | HCT116 | RAJ1 | RAMOS | SNU398 | Namalwa | H1299 |
| A | [structure] | 3676 | 5454 | >10000 | >10000 | 1864 | >10000 | 3158 |
| B | [structure] | >10000 | >10000 | 5395 | 5300 | >10000 | 5629 | ND |
| C | [structure] | 4032 | 4574 | >10000 | 566 | 1718 | 574 | ND |

-continued

The caspase potency (EC$_{50}$) are summarized in Table I:

| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| D | 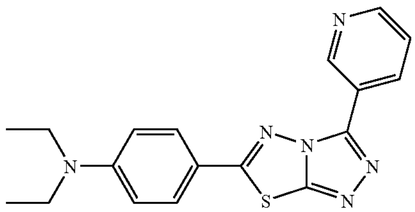 | ND | ND | 5071 | 1103 | ND | 2475 | ND |
| E | 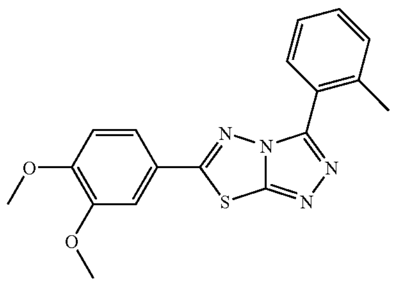 | 561 | 5025 | 274 | 235 | 507 | 253 | 3005 |
| F | 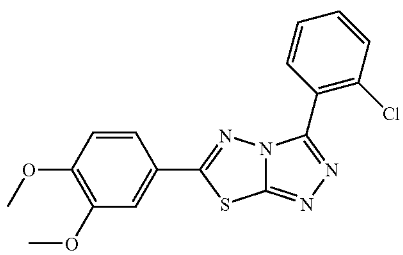 | 2687 | 5155 | 5266 | 5301 | 4459 | 5316 | 5309 |
| G | 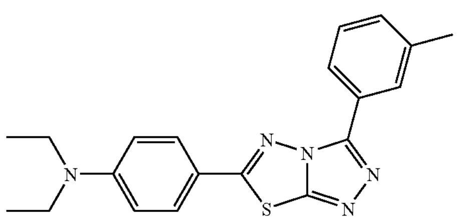 | ND | ND | 2933 | 2238 | ND | 2350 | ND |
| H | 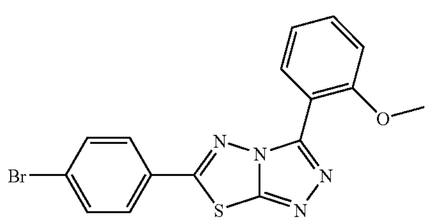 | 563 | 537 | 501 | 253 | 261 | 344 | 733 |
| I | 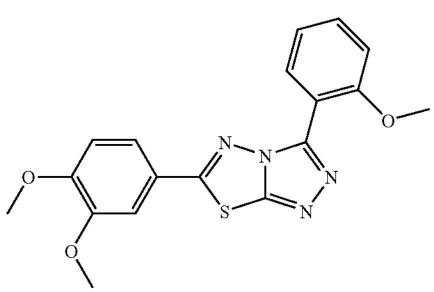 | 563 | 523 | 521 | 349 | 300 | 412 | 808 |

-continued
The caspase potency (EC$_{50}$) are summarized in Table I:
| | | EC$_{50}$ (nM) | | | | | | |
|---|---|---|---|---|---|---|---|---|
| Entry | Structure | T47D | HCT116 | RAJ1 | RAMOS | SNU398 | Namalwa | H1299 |
| J | 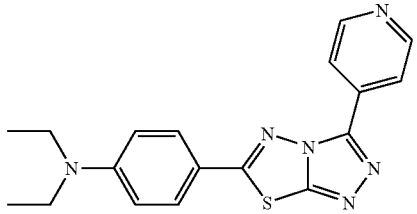 | ND | ND | 1059 | 524 | ND | 598 | ND |
| K | 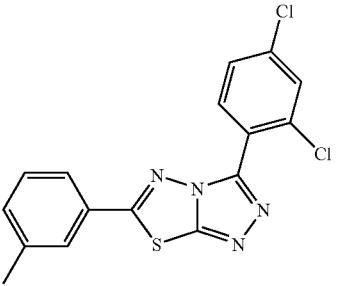 | 607 | 661 | 505 | 387 | 482 | 469 | ND |
| L | 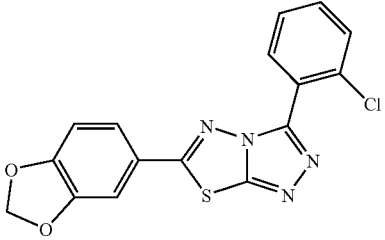 | 2624 | >10000 | >10000 | >10000 | >10000 | >10000 | >10000 |
| M | 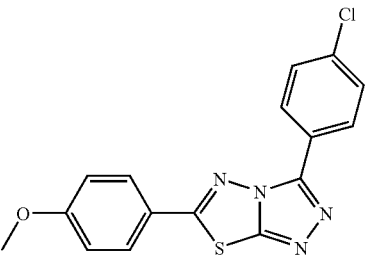 | 4481 | >10000 | >10000 | >10000 | >10000 | >10000 | 5047 |
| N | 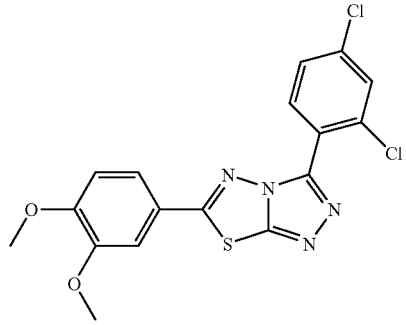 | 5016 | >10000 | >10000 | 5781 | >10000 | 5512 | >10000 |

-continued
The caspase potency (EC$_{50}$) are summarized in Table I:
| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| O | 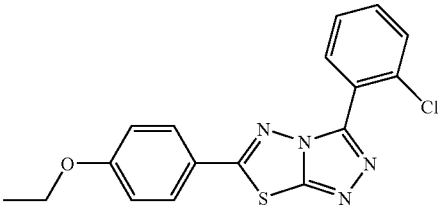 | 2434 | >10000 | >10000 | >10000 | >10000 | >10000 | >10000 |
| P | 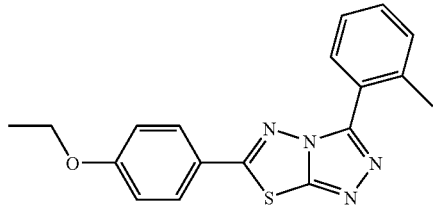 | 2372 | 5752 | >10000 | 5710 | 5548 | >10000 | 5144 |
| Q | 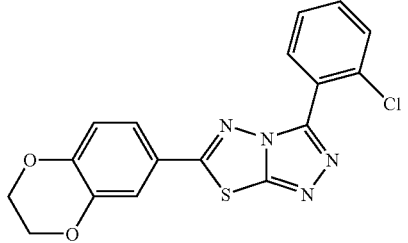 | 2448 | 2671 | 688 | 532 | 2115 | 552 | ND |
| R | 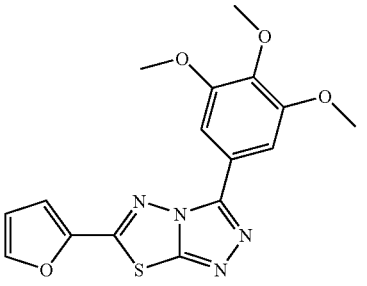 | 203 | 216 | 253 | 241 | 183 | 244 | ND |
| S | 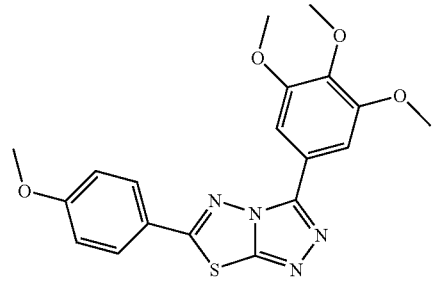 | 2419 | >10000 | >10000 | 2442 | >10000 | >10000 | ND |

-continued

The caspase potency (EC$_{50}$) are summarized in Table I:

| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| T | 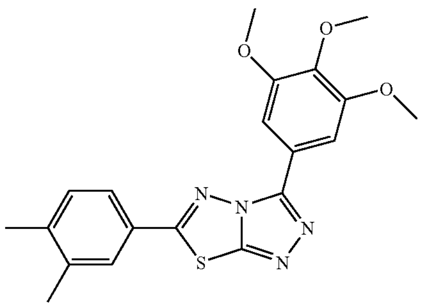 | 517 | 336 | 490 | 314 | 297 | 611 | ND |
| U | 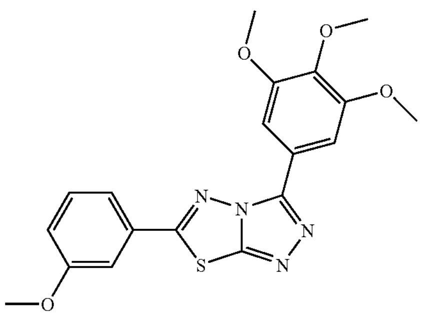 | 2736 | >10000 | >10000 | >10000 | >10000 | >10000 | ND |
| V | 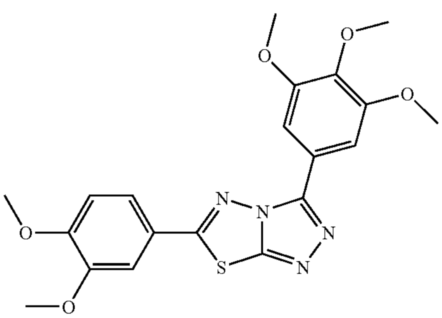 | >10000 | >10000 | >10000 | 2321 | >10000 | >10000 | ND |
| W | 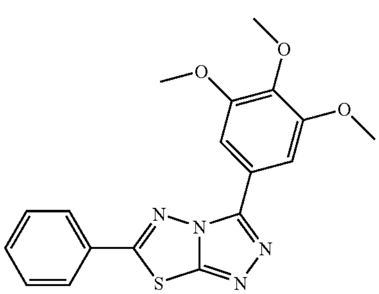 | 5042 | >10000 | >10000 | >10000 | >10000 | >10000 | ND |

-continued
The caspase potency (EC$_{50}$) are summarized in Table I:
| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| X | 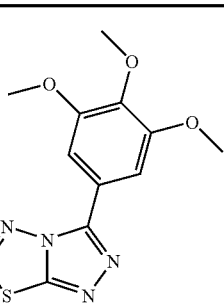 | 3606 | 2357 | >10000 | >10000 | 2006 | >10000 | ND |
| Y | 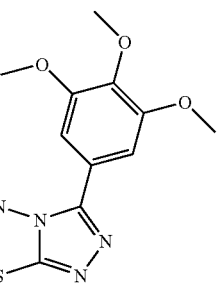 | 5441 | >10000 | >10000 | >10000 | >10000 | >10000 | ND |
| Z | 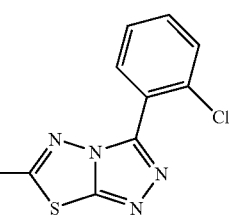 | ND | ND | 1558 | 1018 | ND | 963 | ND |
| A1 | 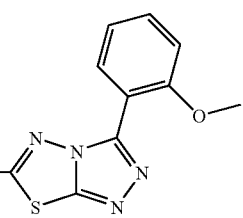 | 662 | 321 | 198 | 115 | 160 | 92 | ND |
| B1 | 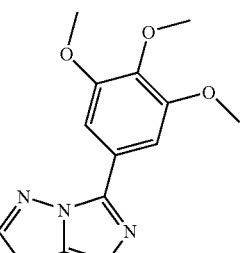 | 1545 | 647 | 678 | 379 | 494 | 356 | ND |

-continued

The caspase potency (EC$_{50}$) are summarized in Table I:

| Entry | Structure | EC$_{50}$ (nM) ||||||| 
| | | T47D | HCT116 | RAJ1 | RAMOS | SNU398 | Namalwa | H1299 |
|---|---|---|---|---|---|---|---|---|
| C1 | | ND | ND | >10000 | 5178 | ND | 5305 | ND |
| D1 | | 1392 | 2268 | 1410 | 1249 | 1647 | 1286 | ND |
| E1 | | 1086 | 1195 | 573 | 325 | 556 | 327 | ND |
| F1 | | 666 | 1723 | 1019 | 712 | 751 | 734 | ND |
| G1 | | 584 | 1381 | 627 | 575 | 455 | 593 | ND |
| H1 | | ND | Nd | 4943 | 3919 | ND | 2663 | ND |

-continued
The caspase potency (EC$_{50}$) are summarized in Table I:
| Entry | Structure | EC$_{50}$ (nM) ||||||| 
|---|---|---|---|---|---|---|---|---|
| | | T47D | HCT116 | RAJ1 | RAMOS | SNU398 | Namalwa | H1299 |
| I1 | 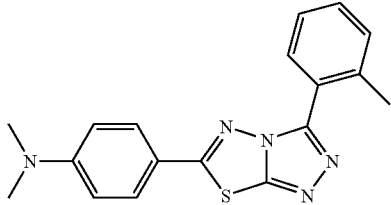 | 864 | 1328 | 634 | 558 | 596 | 510 | ND |
| J1 | 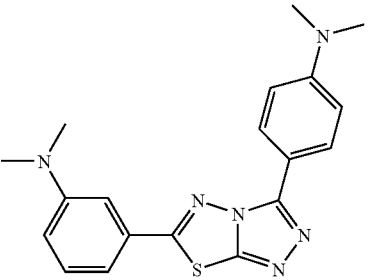 | ND | ND | >10000 | 5327 | ND | 5526 | ND |
| K1 | 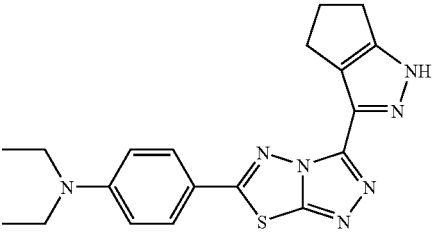 | 636 | 1016 | 617 | 585 | ND | 580 | ND |
| L1 | 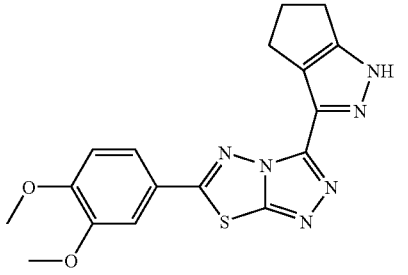 | 2427 | 2757 | 2694 | 1735 | ND | 1309 | ND |
| M1 | 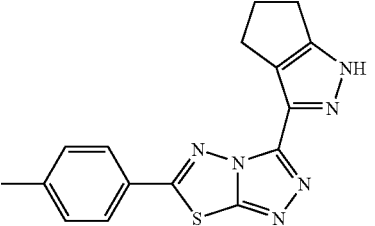 | 395 | 67 | 81 | 40 | 34 | 39 | ND |

-continued

The caspase potency (EC$_{50}$) are summarized in Table I:

| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| 1 | 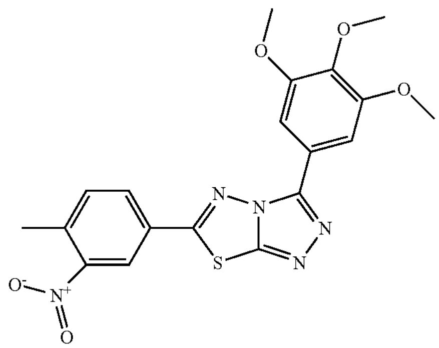 | >10000 | >10000 | ND | ND | >10000 | >10000 | ND |
| 2 | 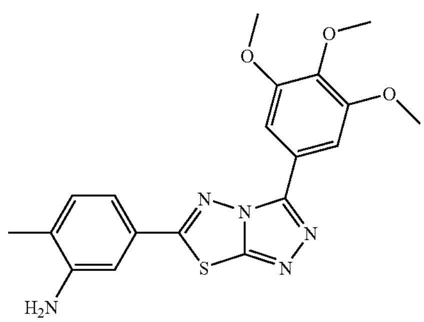 | 1621 | 1315 | ND | ND | 645 | 626 | ND |
| 3 | 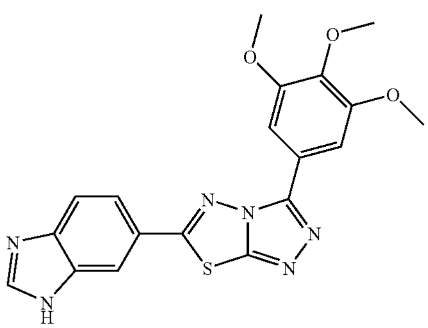 | >10000 | >10000 | ND | ND | >10000 | >10000 | ND |
| 4 | 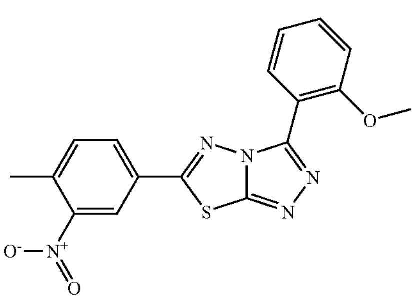 | >10000 | >10000 | ND | ND | >10000 | >10000 | ND |

-continued

The caspase potency (EC$_{50}$) are summarized in Table I:

| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| 5 | 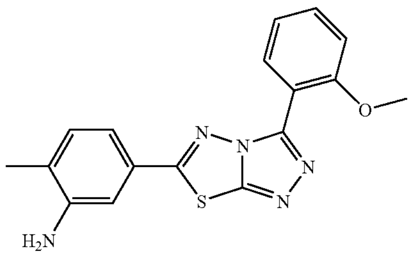 | 121 | 40 | ND | ND | 33 | 18 | ND |
| 6 | 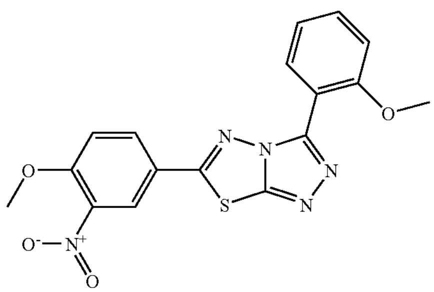 | >10000 | >10000 | ND | ND | >10000 | >10000 | ND |
| 7 | 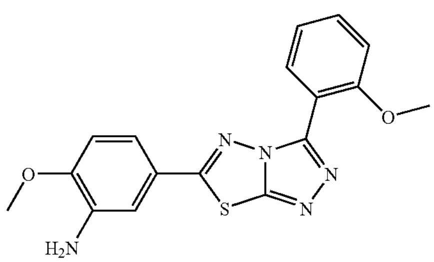 | 284 | 21 | ND | ND | 19 | 18 | ND |
| 8 | 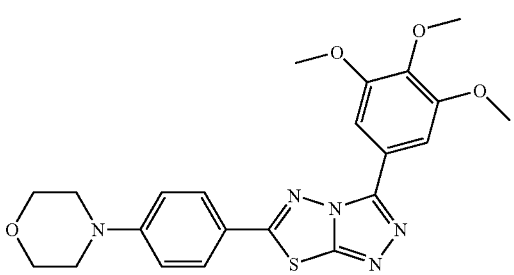 | >10000 | >10000 | ND | ND | >10000 | >10000 | ND |

-continued
The caspase potency (EC$_{50}$) are summarized in Table I:
| Entry | Structure | EC$_{50}$ (nM) | | | | | | |
|---|---|---|---|---|---|---|---|---|
| | | T47D | HCT116 | RAJ1 | RAMOS | SNU398 | Namalwa | H1299 |
| 9 | 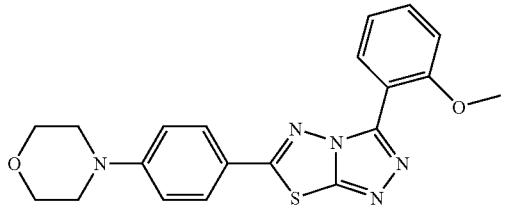 | 1265 | 2635 | ND | ND | 2315 | 2377 | ND |
| 10 | 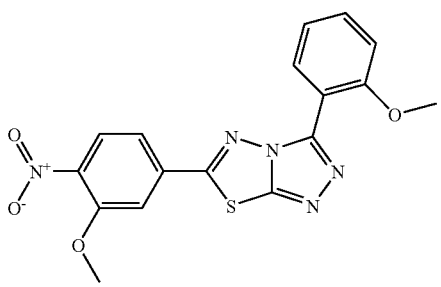 | >10000 | >10000 | ND | ND | >10000 | >10000 | ND |
| 11 | 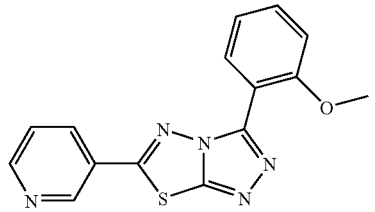 | >10000 | >10000 | ND | ND | >10000 | >10000 | ND |
| 12 | 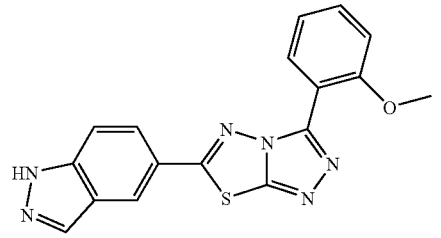 | 1178 | 1170 | ND | ND | 571 | 649 | ND |
| 13 | 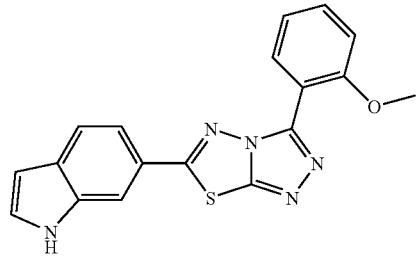 | 967 | 663 | ND | ND | 146 | 155 | ND |
ND: Not determined.

Thus, 6-(3,4-dimethoxyphenyl)-3-(2-methoxyphenyl)-[1,2,4]triazolo[3,4-b][1,3,4]thiadiazole (Example I) and analogs are identified as potent caspase cascade activators and inducers of apoptosis in several tumor cells. Importantly, these compounds are active in human Burkitt's lymphoma cell line Namalwa, human lymphoma cell line Raji, and human B cell lymphoblastoid cell line Ramos, three cell lines that are known to have deregulated cMyc.

EXAMPLE 15

Identification of 6-(3,4-Dimethoxyphenyl)-3-(2-methoxyphenyl)-[1,2,4]triazolo[3,4-b][1,3,4]thiadiazole as Antineoplastic Compound that Inhibits Cell Proliferation ($GI_{50}$)

Human breast cancer cell lines T-47D, MX1 and MDAMB435, human colon carcinoma cell line HCT116, human leukemia cell line K562, human lymphoma cell line Raji, human B cell lymphoblastoid cell line Ramos, and human Burkitt's lymphoma cell line Namalwa were grown and harvested as in Example 14. An aliquot of 90 μL of cells ($4.4 \times 10^4$ cells/mL) was added to a well of a 96-well microtiter plate containing 5 μL of a 10% DMSO in RPMI-1640 media solution containing 10 nM to 100 μM of 6-(3,4-dimethoxyphenyl)-3-(2-methoxyphenyl)-[1,2,4]triazolo[3,4-b][1,3,4]thiadiazole (1 nM to 10 μM final). An aliquot of 45 μL of cells was added to a well of a 96-well microtiter plate containing 5 μL of a 10% DMSO in RPMI-1640 media solution without compound as the control sample for maximal cell proliferation ($L_{Max}$). The samples were mixed by agitation and then incubated at 37° C. for 48 h in a 5% $CO_2$-95% humidity incubator. After incubation, the samples were removed from the incubator and 25 μL of CellTiter-Glo™ reagent (Promega) was added. The samples were mixed by agitation and incubated at room temperature for 10-15 min. Plates were then read using a luminescent plate reader (Model SPECTRAfluor Plus, Tecan) to give $L_{test}$ values.

Baseline for $GI_{50}$ (dose for 50% inhibition of cell proliferation) of initial cell numbers was determined by adding an aliquot of 45 μL of cells or 45 μL of media, respectively, to wells of a 96-well microtiter plate containing 5 μL of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 25 μL of CellTiter-Glo™ reagent (Promega) was added. The samples were mixed by agitation and incubated at 37° C. for 10-15 min at room temperature in a 5% $CO_2$-95% humidity incubator. Fluorescence was read as above, ($L_{Start}$) defining luminescence for initial cell number used as baseline in $GI_{50}$ determinations.

Calculation:

$GI_{50}$ (dose for 50% inhibition of cell proliferation) is the concentration where $[(L_{Test}-L_{Start})/(L_{Max}-L_{Start})]=0.5$.

The $GI_{50}$ (nM) are summarized in Table II:

TABLE II $GI_{50}$ in Cancer Cells $GI_{50}$ (nM)

| Entry | T47D | HCT 116 | MX1 | MDA MB 435 | Namalwa | Raji | Ramos | K562 |
|---|---|---|---|---|---|---|---|---|
| A | 2731 | ND | 4084 | 253 | ND | ND | ND | ND |
| C | 900 | ND | 9000 | ND | ND | ND | ND | ND |
| E | 3853 | 6223 | 4000 | 894 | 7867 | 9401 | 3000 | 2487 |
| F | 4033 | 7919 | 4000 | 1074 | 9037 | 8000 | 4000 | 2726 |
| H | 217 | 844 | 400 | 48 | 520 | 700 | 120 | 626 |
| I | 261 | 2000 | 1027 | 136 | 2000 | 2000 | 2000 | 2075 |
| K | ND | 400 | ND | ND | 559 | 500 | 123 | 379 |
| P | ND | >10000 | ND | ND | 7687 | 9739 | 6425 | 3268 |
| Q | ND | 6038 | ND | ND | 2044 | 6727 | 1303 | 1877 |
| R | ND | 1502 | ND | ND | 450 | 651 | 442 | 150 |
| S | ND | >10000 | ND | ND | >10000 | >10000 | 4992 | 1457 |
| T | ND | 906 | ND | ND | 500 | 559 | 137 | 131 |
| U | ND | >10000 | ND | ND | >10000 | 4640 | 2692 | 2769 |
| V | ND | 5000 | ND | ND | >10000 | 5000 | 3646 | 1596 |
| A1 | ND | 2499 | ND | ND | 126 | 966 | 58 | 124 |
| B1 | ND | 1000 | ND | ND | 253 | 549 | 119 | 303 |
| D1 | ND | 6830 | ND | ND | 1132 | 2595 | 647 | 1024 |
| E1 | ND | 2043 | ND | ND | 167 | 519 | 146 | 332 |
| F1 | ND | 694 | ND | ND | 372 | 801 | 113 | 303 |
| G1 | ND | 492 | ND | ND | 149 | 405 | 41 | 155 |
| I1 | ND | 1192 | ND | ND | 142 | 253 | 93 | 350 |
| K1 | 167 | 497 | ND | ND | 138 | ND | ND | ND |
| M1 | 200 | 89 | ND | ND | 16 | ND | ND | ND |
| 5 | 22 | 107 | ND | ND | 21 | ND | ND | ND |
| 7 | 100 | 83 | ND | ND | 14 | ND | ND | ND |

ND, Not determined.

Thus, 6-(3,4-dimethoxyphenyl)-3-(2-methoxyphenyl)-[1,2,4]triazolo[3,4-b][1,3,4]thiadiazole (Example I) and analogs are identified as antineoplastic compound that inhibits cell proliferation in several tumor cell lines.

Having now fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed is:

1. A pharmaceutical composition comprising a pharmaceutically acceptable carrier and a compound selected from the group consisting of:
   6-(4-Methoxy-3-nitrophenyl)-3-(2-methoxyphenyl)-[1,2,4]triazolo[3,4-b][1,3,4]thiadiazole;
   6-(3-Amino-4-methoxyphenyl)-3-(2-methoxyphenyl)-[1,2,4,]triazolo[3,4-b][1,3,4]thiadiazole;
   and 6-(3-Methoxy-4-nitrophenyl)-3-(2-methoxyphenyl)-[1,2,4]triazolo[3,4-b][1,3,4]thiadiazole;
or a pharmaceutically acceptable salt thereof.

2. A compound selected from the group consisting of:
   6-(4-Methoxy-3-nitrophenyl)-3-(2-methoxyphenyl)-[1,2,4]triazolo[3,4-b][1,3,4]thiadiazole;
   6-(3-Amino-4-methoxyphenyl)-3-(2-methoxyphenyl)-[1,2,4,]triazolo[3,4-b][1,3,4]thiadiazole;
   and 6-(3-Methoxy-4-nitrophenyl)-3-(2-methoxyphenyl)-[1,2,4]triazolo[3,4-b][1,3,4]thiadiazole;
or a pharmaceutically acceptable salt thereof.

3. A method of treating cancer comprising administering to a mammal in need of such treatment an effective amount of a composition of claim 1, wherein the cancer is selected from breast carcinoma, colon carcinoma, liver cancer, acute lymphocytic leukemia, and chronic lymphocytic leukemia.

4. A method of treating cancer comprising administering to a mammal in need of such treatment an effective amount of a compound of claim 2, wherein the cancer is selected from breast carcinoma, colon carcinoma, liver cancer, acute lymphocytic leukemia, and chronic lymphocytic leukemia.

* * * * *